United States Patent
Swetledge

(10) Patent No.: US 8,778,606 B2
(45) Date of Patent: Jul. 15, 2014

(54) AT-HOME CANCER TEST

(76) Inventor: John A. Swetledge, Walker, LA (US)

( * ) Notice: Subject to any disclaimer, the term of this patent is extended or adjusted under 35 U.S.C. 154(b) by 1009 days.

(21) Appl. No.: 11/493,651

(22) Filed: Jul. 27, 2006

(65) Prior Publication Data

US 2006/0257954 A1 Nov. 16, 2006

Related U.S. Application Data

(63) Continuation-in-part of application No. 10/376,673, filed on Mar. 4, 2003, now abandoned.

(51) Int. Cl.
| | |
|---|---|
| *C12Q 1/68* | (2006.01) |
| *G01N 1/00* | (2006.01) |
| *G01N 21/00* | (2006.01) |
| *G01N 21/75* | (2006.01) |
| *G01N 33/48* | (2006.01) |
| *G01N 33/53* | (2006.01) |
| *G01N 33/567* | (2006.01) |
| *G01N 33/574* | (2006.01) |

(52) U.S. Cl.
USPC .............. 435/4; 435/7.1; 435/7.21; 435/7.23; 436/63; 436/64; 436/164; 436/174

(58) Field of Classification Search
None
See application file for complete search history.

(56) References Cited

U.S. PATENT DOCUMENTS

| | | | | |
|---|---|---|---|---|
| 5,674,983 | A * | 10/1997 | Blithe et al. | 530/398 |
| 6,025,149 | A * | 2/2000 | Cuckle et al. | 435/7.94 |
| 2002/0123671 | A1* | 9/2002 | Haaland | 600/300 |
| 2002/0160525 | A1* | 10/2002 | Kang et al. | 436/518 |

FOREIGN PATENT DOCUMENTS

| | | |
|---|---|---|
| WO | WO 96/29430 | 9/1996 |
| WO | WO 01/64941 | 9/2001 |

OTHER PUBLICATIONS

Saller et al., "Testicular Cancer Secretes Intact Human Gonadotropin (hCG) and Its Free -Subunit:Evidence That hCG (+hCG−) Assays are the Most Reliable in Diagnosis and Follow-Up," Clinical Chemistry (1990), Vo. 36, No. 2, pp. 234-239.
Tanaka et al., "Improved Methods for Detecting -Core in Normal and Cancer Patient Urines," Clinical Chemistry (1994), vol. 40, No. 12, pp. 2317-2318.
Motoo et al., "Urinary gonadotropin peptide as acute phase reactant: transient elevation after operation for digestive diseases," European Journal of Endocrinology (1999), vol. 140, pp. 555-560.
Nishimura et al., "Enzyme Immunoassay of Urinary -Core Fragment of Human Chorionic Gonadotropin as a Tumor Marker for Ovarian Cancer," Methods in Molecular Medicine (J.S. Bartlett, ed.), Humana Press, Totowa, New Jersey (2000), pp. 135-141.
Cole et al., "Utility of Commonly Used Commercial Chorionic Gonadotropin Immunoassays in the Diagnosis and Management of Trophoblastic Diseases," Clinical Chemistry (2001), vol. 47, No. 2, pp. 308-315.
Cat. No, 9043-C, "Free -HCG (f -hCG) Chemiluminescence Immunoassay," Diagnostic Automation, Inc., Calabassas, California, Jul. 13, 2006, published at www.rapidtest.com/free/%20B%20HCG_9043-C.doc., 2 pages.

\* cited by examiner

*Primary Examiner* — Alana Harris Dent
(74) *Attorney, Agent, or Firm* — Richard C. Litman

(57) ABSTRACT

The at home cancer test permits a layperson to qualitatively test for the presence of carcinoma in the privacy of their home. The test includes a test strip coated or impregnated with at least one monoclonal antibody that binds to β-hCG/CGH found in the patient's urine, together with a chromophore that provides a color indicator when such binding takes place. The at-home cancer test may comprise a kit containing one or more of the following: a test strip with a tab that can be gripped by the user while the strip is placed in a stream of urine; a cup for collecting urine and a test strip that may be partially immersed in the cup; and a cup for collecting urine, a test strip, and a medicine dropper or pipette for transferring the urine to the test strip.

8 Claims, 1 Drawing Sheet

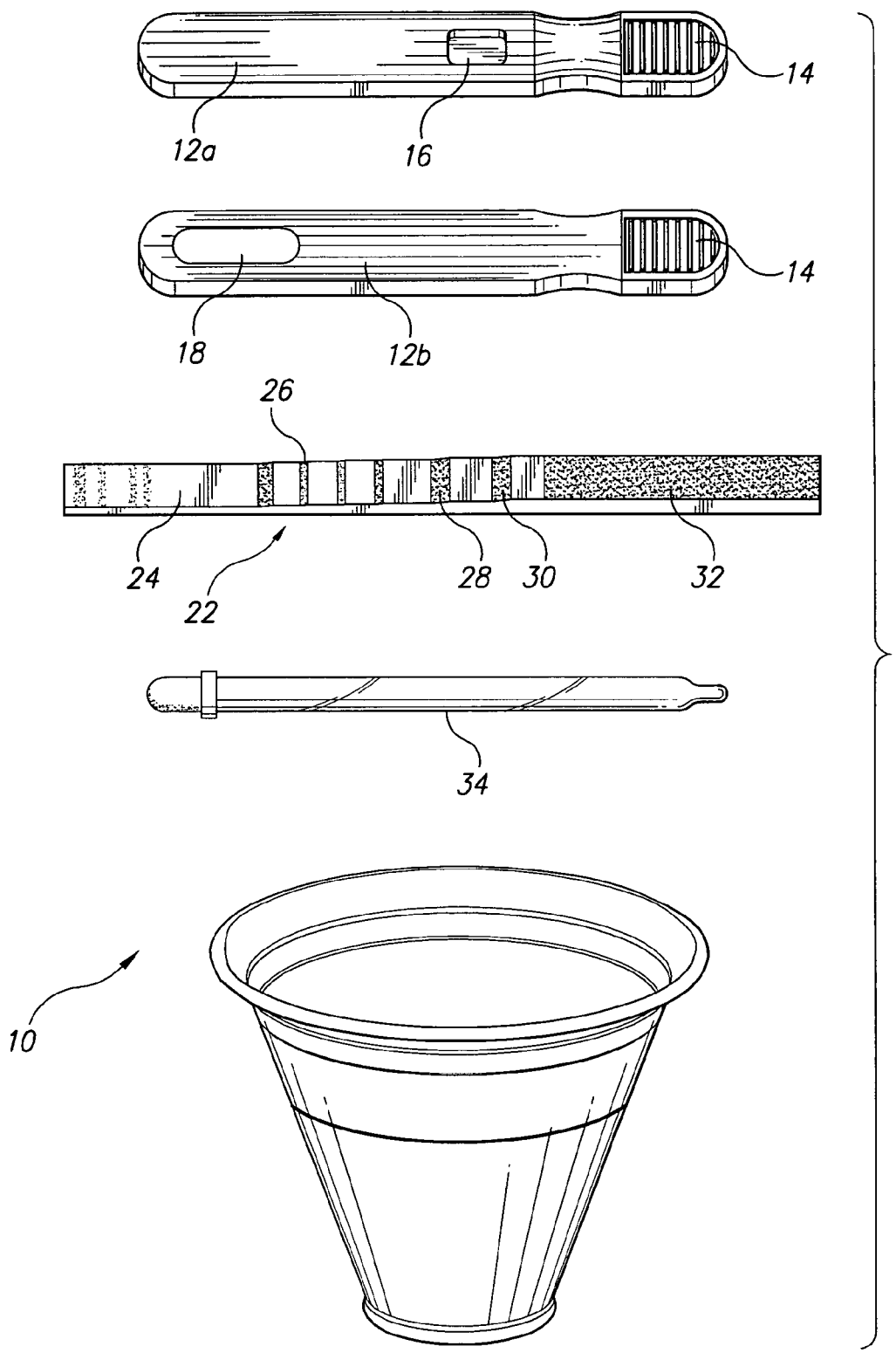

AT-HOME CANCER TEST

CROSS-REFERENCE TO RELATED APPLICATIONS

This is a continuation-in-part of my prior application Ser. No. 10/376,673, filed Mar. 4, 2003 now abandoned.

BACKGROUND OF THE INVENTION

1. Field of the Invention

The present invention relates to medical testing devices, and particularly to an at-home cancer test that can be used by the layperson to obtain a qualitative indication of the presence of carcinoma.

2. Description of the Related Art

Cancer is a prevalent disease in modern society that often proves fatal. Most cancers are, however, potentially curable if diagnosed at an early stage in the disease. The American Cancer Society has identified seven major warning signs of cancer, including a change in bowel or bladder habits; a sore that does not heal; unusual bleeding or discharge; a lump in the breast or other parts of the body; chronic indigestion or difficulty in swallowing; obvious changes in a wart or mole; and persistent coughing or hoarseness.

While providing useful guidelines, it is often difficult for many lay persons to apply the signs to changes in their own bodies due to a lack of objectivity, a lack of sensitivity, the gradual onset of changes, etc. For example, in the case of breast cancer, the hallmark diagnostic sign is the persistence of a dominant mass (i.e., a hard mass) over time. Many women, however, are unable to effectively palpate their own breasts, either through lack of proper training in the procedure, the presence of benign cysts in large pendulous breasts (e.g., fibrocystic disease), qualitative judgments as to the hardness or softness of a mass, apparent shifts in the location of the mass, etc. Similar problems are experienced by men in palpation for testicular cancer, a process often neglected due to its distasteful nature.

The lay person who cannot effectively perform a self-evaluation, but is concerned with the risk of developing cancer, is left with no choice but to visit a doctor or other medical professional, often with great frequency and at the risk of developing a "Peter and the Wolf" syndrome, or incurring the expense of medical testing, such as x-rays, aspirations, biopsies, enzyme assays, antibody titers, etc.

There are many people who fall into certain well-defined profiles that render them more at risk to develop certain forms of cancer than the general population. For example, certain women with large breasts, a Semitic ethnic background, and a family history of breast cancer are apt to be at higher risk for developing breast cancer than the general population. Moreover, persons who have been treated for cancer that has gone into remission need to be vigilant in promptly detecting a recurrence of the cancer. In each of these cases, early detection of the cancer is the key to effective and potentially curative treatment.

Tanaka et al. report studies detecting β-core from Urinary Gonadotropin Peptides (UGP) in *Clinical Chemistry*, Vol. 4.0, No. 12, pp. 2317-18 (1994) using three kits, one of which was released for research purposes, and another of which was produced in Japan but not yet approved for use by the Japanese government. The structure and method of use of the kits is not described. However, it is clear that the kits are immunoassay kits. As noted by Cole et al. in *Clinical Chemistry*, Vol. 47, No. 2, pp. 308-315 (1994), such immunoassays are usually quantitative tests, often use polyclonal antibodies, are automated, require considerable sample preparation, are performed in laboratories, and are noted for the complexity of the procedure, the extensive pipetting, their relative imprecision, and time-consuming procedures. Such considerations generally militate against the use of immunoassays for home use by laypersons. For similar reasons, the immunoassays described by Nishimura et al. in *Molecular Medicine, Vol. 39, Ovarian Cancer:Methods and Protocols* pp. 135-141 (Humanas Press, Inc., Totowa, N.J.; by Saller et al. in *Clinical Chemistry* 36(2): 234-239 (February 1990); by WO 96/29430, published Sep. 26, 1996; and by WO 01/64941, published Feb. 29, 2000, are not appropriate for home use, as they are multi-step procedure involving multiple reagents and automated processes more suited for the laboratory than by the lay person.

For these reasons, a quick, painless, easy-to-use test kit that the lay person might use in the privacy of his or her home to provide a qualitative early warning signal of the presence of carcinoma so that the lay person can feel comfortable in seeking appropriate confirmation and treatment from a medical professional is desired. None of the above inventions, publications, and patents, taken either singly or in combination, is seen to describe the instant invention as claimed. Thus, an at home cancer test solving the aforementioned problems is desired.

SUMMARY OF THE INVENTION

The at home cancer test permits a layperson to qualitatively test for the presence of carcinoma in the privacy of their home. The test includes a test strip coated or impregnated with at least one monoclonal antibody that binds to β-hCG/CGH found in the patient's urine, together with a chromophore that provides a color indicator when such binding takes place. The at-home cancer test may comprise a kit containing one or more of the following: a test strip with a tab that can be gripped by the user while the strip is placed in a stream of urine; a cup for collecting urine and a test strip that may be partially immersed in the cup; and a cup for collecting urine, a test strip, and a medicine dropper or pipette for transferring the urine to the test strip.

The at-home cancer test is non-specific, and is not definitive, but provides the lay person with a simple, quick, qualitative test for the presence of carcinoma that alerts the lay person to check with a qualified medical practitioner for more definitive testing for the presence or absence of cancer.

These and other features of the present invention will become readily apparent upon further review of the following specification and drawings.

BRIEF DESCRIPTION OF THE DRAWINGS

The sole FIGURE is an exploded view showing components that may be optionally included in an at-home cancer test kit according to the present invention.

DETAILED DESCRIPTION OF THE PREFERRED EMBODIMENTS

The present invention is an at-home cancer test that can be used by the layperson in the privacy of his or her home to provide a simple, quick, qualitative indication of the possible presence of carcinoma. The at-home cancer test is premised upon the observation that testicular cancer, choriocarcinomas, and many other, if not all, forms of cancer result in the production of Human Chorionic Gonadotropin (HCG or hCG) hormone, also known as Chorionic Gonadotrophic Hormone (CGH), which can be detected in the urine. HCG is also present during pregnancy. Many home pregnancy test kits are based upon a test strip impregnated with monoclonal antibodies, at least one of which binds to hCG to produce a color change.

However, hCG is a glycoprotein hormone that includes α and β subunits, which are dissimilar and are noncovalently joined in hCG. The α subunit is not unique to hCG, and may be found in other hormones, such as LH, FSH, and TSH. The β subunit is, however, specific to hCG. Since the monoclonal antibodies used in home pregnancy test kits bind to hCG generally, and are not specific to the β subunit, a false positive finding of hCG sometimes occurs with home pregnancy test kits.

The at-home cancer test avoids this problem by impregnating the test strip with at least one monoclonal antibody that binds to the β subunit of hCG as the antigen.

The at-home cancer test strip is made by compressing nonwoven fibers, e.g., rayon polyester, into strips or pads either mechanically or thermally. The strips may then be coated with latex, and bands of monoclonal antibodies may be coated onto the strip. The bands include at least one monoclonal antibody that binds specifically to the β subunit of hCG. The bands may include monoclonal antibodies that bind to another component typically found in urine, such as immunoglobulin G (IgC), which acts as a control to indicate that the strip is still fresh or functional. The bands are separated into a test band and a control band. The test band may include a chemiluminescent agent, such as luminol, a fluorescent marker, a chromophore, or any other color change indicator or substrate to provide a color change in the test band when the monoclonal antibody binds to the β subunit of hCG. Alternatively, the strip may be coated with more than one band of monoclonal antibodies specific to the β subunit antigen of hCG so that the two antibodies bind to the β subunit sequentially, forming a sandwich with resulting color change.

The resulting test strip may be encased in a decorative plastic housing having a test window and a control window for observation of the color changes, if desired.

Many monoclonal antibodies that bind to the β subunit of hCG have long been known to those of ordinary skill in the art. For example, an article by Y. Motoo et al. in the *European journal of Endocrinology*, Vol. 140, pp. 555-560 (1999) describes a UGP assay that uses monoclonal antibody B210, which reacts only with the core fragment of urinary hCGβ. A catalog description from Diagnostic Automation, Inc. for a "Free β-HCG (fβ-hCG) Chemiluminescence Immunoassay", published on the Internet at least as of Jul. 13, 2006, describes an immunoassay performed on spot plates that uses two different monoclonal antibodies that bind specifically to the free β subunit of hCG. The foregoing examples simply illustrate a few monoclonal antibodies that may be used in a test strip according to the present invention for purposes of enablement, and not by way of limitation, so that it will be understood that any monoclonal antibody that binds to the β subunit of hCG may be used in the test strip, depending upon the configuration.

It will be understood that the test strip may be configured to indicate a positive test for the β subunit of hCG only when the concentration of hCG in the urine exceeds a predetermined limit by adjusting the concentration of the monoclonal antibodies, by the choice of color change indicator, by the length of travel or separation of the bands, or by any other technique known to those skilled in the art of making test strips.

The sole drawing FIGURE shows various combinations of components that may be included in an at-home cancer test kit, designated generally as 10 in the drawing, according to the present invention. The kit 10 may include a handheld test strip having a top surface 12a and a bottom surface 12b. The test strip has a liquid impervious tab 14 at one end so that it may be held by the layperson in a stream of urine. A test or result window 16 is formed in top surface 12a, and a control window 18 is formed in bottom surface 12b. The strip is used by grasping tab 14, inserting the body of the strip into a stream of urine, checking for a color change in control window 18 to ascertain whether the strip is still functional, and checking for a color change in the result window 16 to check for the presence of hCG, indicating possible carcinoma.

Alternatively, the kit 10 may include a urine collection cup 20 and a test strip 22 that may be at least partially immersed in the urine. Test strip 22 may include a region of absorbent pad 24, an immersion line 26 indicating the depth of insertion of the strip into cup 20, a test band 28 that changes color when hCG is present, a control band 30 that changes color to indicate the strip is still functional, and a thumb grip 32 for holding the strip while immersing the strip in cup 20.

In another alternative, the kit 10 may include a medicine dropper or pipette 34 that can be used in conjunction with cup 20 and test strip 22, so that the layperson collects urine in the cup 20 and transfers a specified number of drops to the absorbent pad 24 of test strip 22.

Of course, the kit 10 may include all of the aforementioned components to offer the layperson a choice of methods for performing the at-home cancer test. The kit 10 will also include written instructions on how to use the components, as well as advice to seek professional medical assistance in the event of a positive result.

Thus, the at-home cancer test provides a simple, quick, easy-to-use test that can be used by the lay person in the privacy of his or her home to obtain a qualitative indication of carcinoma as a screening test that should be later confirmed by more definitive laboratory testing.

It is to be understood that the present invention is not limited to the embodiments described above, but encompasses any and all embodiments within the scope of the following claims.

I claim:

1. An at home cancer test, consisting of:
   a test strip made from an absorbent pad;
   a band of monoclonal antibodies coated thereon, the monoclonal antibodies binding only to the β subunit of human chorionic gonadotropin in urine; and
   a color change indicator disposed on the band of monoclonal antibodies, the indicator changing the color of the band upon binding of the monoclonal antibodies to human chorionic gonadotropin, the color change being visible to the naked eye, whereby the test strip is adapted for use by a lay person at home.

2. The at home cancer test according to claim 1, wherein said color change indicator comprises a chemiluminescent agent.

3. The at home cancer test according to claim 1, wherein said color change indicator comprises a fluorescent marker.

4. The at home cancer test according to claim 1, wherein said color change indicator comprises a chromophore.

5. The at home cancer test according to claim 1, wherein said color change indicator comprises a second monoclonal antibody binding to the β subunit of human chorionic gonadotropin and forming a sandwich around the β subunit, producing a color change.

6. The at home cancer test according to claim 1, wherein said test strip has a tab at one end of the strip for holding the strip in a stream of urine.

7. An at-home cancer test kit, consisting of:
a first test strip made from an absorbent pad, the first test strip having a tab at one end of the strip for holding the strip in a stream of urine;
a band of monoclonal antibodies coated thereon, the monoclonal antibodies binding only to the β subunit of human chorionic gonadotropin in the urine; a color change indicator disposed on the band of monoclonal antibodies, the indicator changing the color of the band upon binding of the monoclonal antibodies to human chorionic gonadotropin;
a urine collection cup; and
a second test strip made from an absorbent pad and having a band of monoclonal antibodies coated thereon, the monoclonal antibodies binding only to the β subunit of human chorionic gonadotropin in urine and a color change indicator disposed on the band of monoclonal antibodies, the indicator changing the color of the band upon binding of the monoclonal antibodies to human chorionic gonadotropin, the second test strip being adapted for immersion into urine collected in the cup, whereby a user may elect to hold the first test strip in a stream of urine or immerse the second test strip into the urine collected in the cup, the color change being visible to the naked eye, whereby the first and second test strips are adapted for use by a lay person at home.

8. The at home cancer test kit according to claim 7, further comprising a medicine dropper for transferring the urine collected in the cup to the second test strip.

* * * * *